United States Patent [19]

Yoshioka et al.

[11] Patent Number: 5,511,408
[45] Date of Patent: Apr. 30, 1996

[54] AUTOMATIC CALIBRATING APPARATUS FOR LABORATORY ION CONCENTRATION METER

[75] Inventors: Nobuki Yoshioka; Hiromi Ohkawa, both of Kyoto, Japan

[73] Assignee: Horiba, Ltd., Kyoto, Japan

[21] Appl. No.: 98,508

[22] Filed: Jul. 28, 1993

[30] Foreign Application Priority Data

Jul. 30, 1992 [JP] Japan .............................. 4-059520 U

[51] Int. Cl.⁶ .......................... G01N 37/00; G01N 27/416
[52] U.S. Cl. .......................... 73/1 R; 324/438; 422/67; 422/82.03; 436/43; 204/433
[58] Field of Search ............................. 73/1 R; 324/438, 324/601; 204/153.21, 433; 422/67, 82.03; 436/43, 163, 73, 324

[56] References Cited

U.S. PATENT DOCUMENTS

| | | | |
|---|---|---|---|
| 2,782,151 | 2/1957 | Suthard | 324/438 |
| 3,272,725 | 9/1966 | Garst | 324/438 |
| 3,884,640 | 5/1975 | Lock et al. | 324/438 |
| 3,963,440 | 6/1976 | Stein et al. | 324/439 |
| 4,151,255 | 4/1979 | Capuano et al. | 324/438 |
| 4,512,852 | 4/1985 | Tsuboshima et al. | 422/67 |
| 4,513,280 | 4/1985 | Hannon et al. | 324/438 |
| 4,627,893 | 12/1986 | Cormier et al. | 73/1 R |
| 4,852,385 | 8/1989 | Brinkmann | 73/1 R |
| 4,912,417 | 3/1990 | Gibboney et al. | 324/438 |
| 5,118,628 | 6/1992 | Krumpen et al. | 436/163 |
| 5,124,659 | 6/1992 | Frola et al. | 73/1 R |
| 5,204,264 | 4/1993 | Kaminer | 73/1 R |
| 5,230,863 | 7/1993 | Salpeter | 73/1 R |
| 5,312,528 | 5/1994 | Hoogendijk | 204/153.21 |

FOREIGN PATENT DOCUMENTS

| | | | |
|---|---|---|---|
| 201776 | 11/1986 | European Pat. Off. | 324/438 |
| 2127244 | 11/1972 | Germany | 324/438 |

Primary Examiner—Hezron E. Williams
Assistant Examiner—Daniel S. Larkin
Attorney, Agent, or Firm—Price, Gess & Ubell

[57] ABSTRACT

An automatic calibrating apparatus for a measurement instrument having a sensor member includes a chamber adapted to hold the sensor member during a storage mode. A controller can respond to the presence of the sensor member and automatically wash the sensor member, and subsequently immerse it in a calibration solution. The output reading of the sensor member, along with the temperature, can then be utilized to calibrate the instrument. The sensor member can be subsequently cleansed with a washing fluid so that it is ready for immediate use.

10 Claims, 4 Drawing Sheets

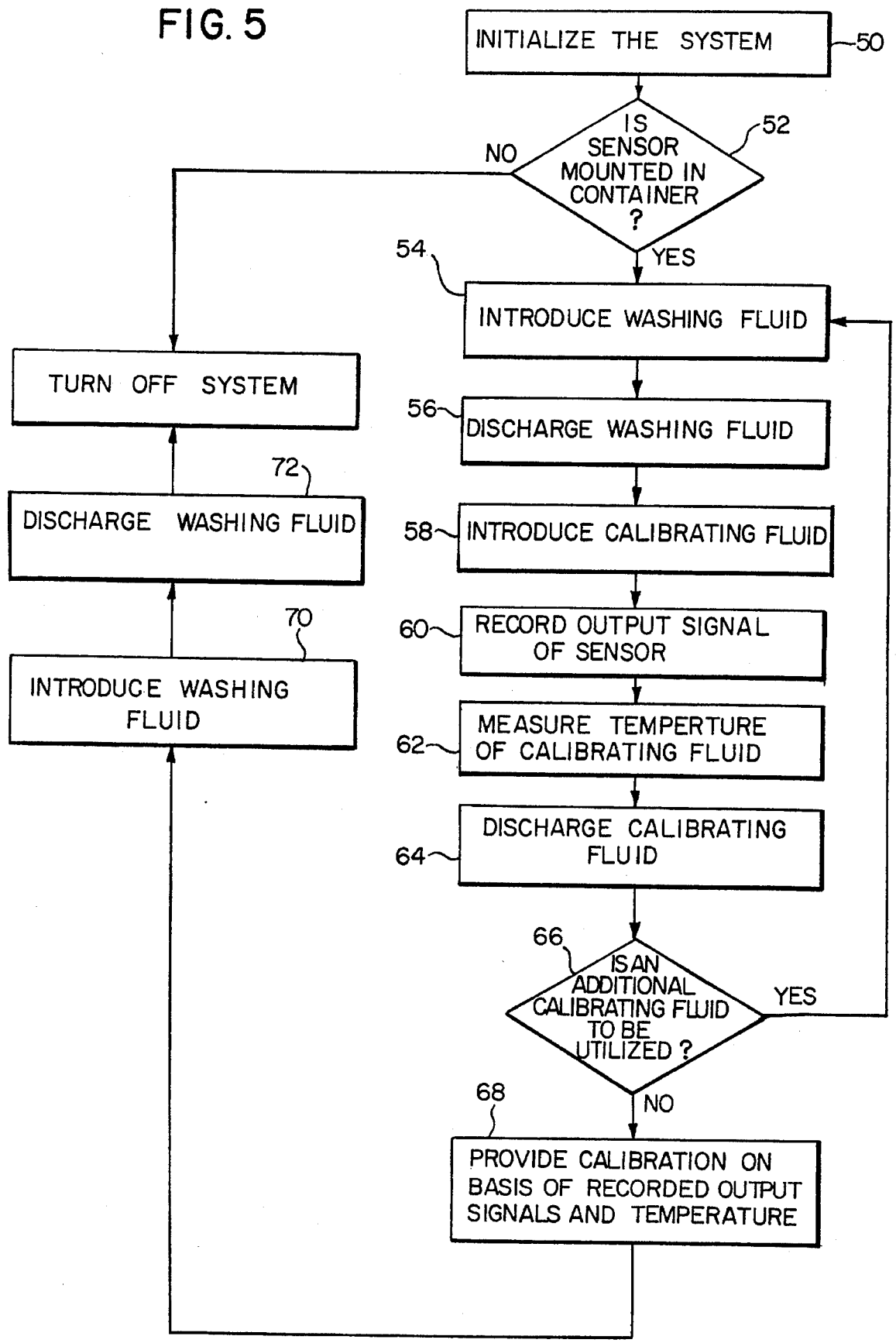

AUTOMATIC CALIBRATING APPARATUS FOR LABORATORY ION CONCENTRATION METER

BACKGROUND OF THE INVENTION

1. Field of the Invention

The present invention is directed to apparatus for the automatic calibration of measuring instruments having a sensor probe that can be subject to changes in output signals and, more particularly, to an automatic calibrating apparatus that can perform the calibration on a sensor probe during a storage mode.

2. Description of Related Art

It is well known that various forms of scientific and measurement instruments require periodic calibration to the sensitivity of various components of the measurement system, such as a sensor probe. For example, a pH meter that is frequently used in laboratories and in field applications can have its electric potential and sensitivity change over a period of time, and also when subjected to various concentrations of solutions. Thus, it is required to periodically calibrate the instrument, or even to calibrate it prior to each measurement.

Referring to FIG. 3(A), an example of a conventional prior art system is disclosed wherein an electrode portion 32 is formed at the front end of an ion concentration measuring portion 31. The electrode portion 32 is washed, for example, by pure or distilled water from an appropriate pure water vessel 33, in order to remove the drops of any liquid that has adhered to the electrode portion 32. After this washing, the electrode portion 32 can be soaked in a calibrating pH standard solution 36 contained in a beaker 35, as shown in FIG. 3(B). The operator then monitors the stabilization of any indicated output value on a visual display portion 38 of the pH meter body 37, as shown in FIG. 4. In addition, the temperature of the calibration solution 36 is measured by means of a thermometer 39. The pH value at that time can be read on a table (not shown). As seen in FIG. 4, a knob or set of knobs 40 on the pH meter body 37 can then be adjusted so that the indicated value of the output display will correspond to the pH value on the reference table.

Frequently, the above procedure steps must be repeated to both reaffirm the value and to ensure an accurate reading exists.

This procedure must be carried out prior to the measurements, or at least on a periodic basis, and has a disadvantage in that it not only increases the measurement time period required, but further requires an expenditure of time, frequently by relatively skilled technicians, with an appropriate cost factor.

The prior art is still seeking to improve the accuracy and calibration procedures utilized for measurement instrumentation such as pH meters.

OBJECTS AND SUMMARY OF THE INVENTION

It is an object of the present invention to provide an automatic calibrating apparatus capable of replacing the conventional manual calibrating operations in an automatic manner during a storage mode or off-time mode of utilization of the measurement instrument. The automatic calibrating apparatus can accommodate a sensor member or probe in an operative condition and will actively interface with the readings of the monitoring system to automatically introduce a washing fluid and discharge the same, and subsequently introduce one or more calibration fluids while measuring both temperature and the calibration values. Calibration fluids are discharged and a final cycle of introducing the washing fluid and discharging the washing fluid that are introduced to cleanse the sensing member and to make it ready for subsequent utilization. The measurement signals from the sensor member, along with the temperature signals, can then be utilized in a calibration program for automatically comparing with stored reference values in look-up tables that can be placed in the memory of the computing system. Any necessary corresponding adjustment of the sensor member can then be accomplished.

In the automatic calibrating apparatus of the present invention, a chamber that is capable of being detachably mounted with, for example, an ion concentration measuring portion of a measuring instrument, can be formed in a configuration compatible to surround the physical dimensions of the sensor member. A controller can operate a fluid changeable oversupply device so that it can be regulated to supply the chamber with both the washing water and calibrating standard solutions in an appointed order, along with a device for recovering any waste liquid from the chamber. For example, in the case of a pH meter, when the pH of the solution is measured, the electrode portion is immersed into the solution. This electrode portion can then be mounted within the chamber during an off-time or storage mode of operation. The chamber is provided with the washing water or fluid and standard calibration solutions in an appointed order to automatically calibrate the pH meter without requiring any operator interface.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 5 is a flow chart of an operation of the calibration system.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an automatic calibrating apparatus that operates during an off-time period.

Figure 1:
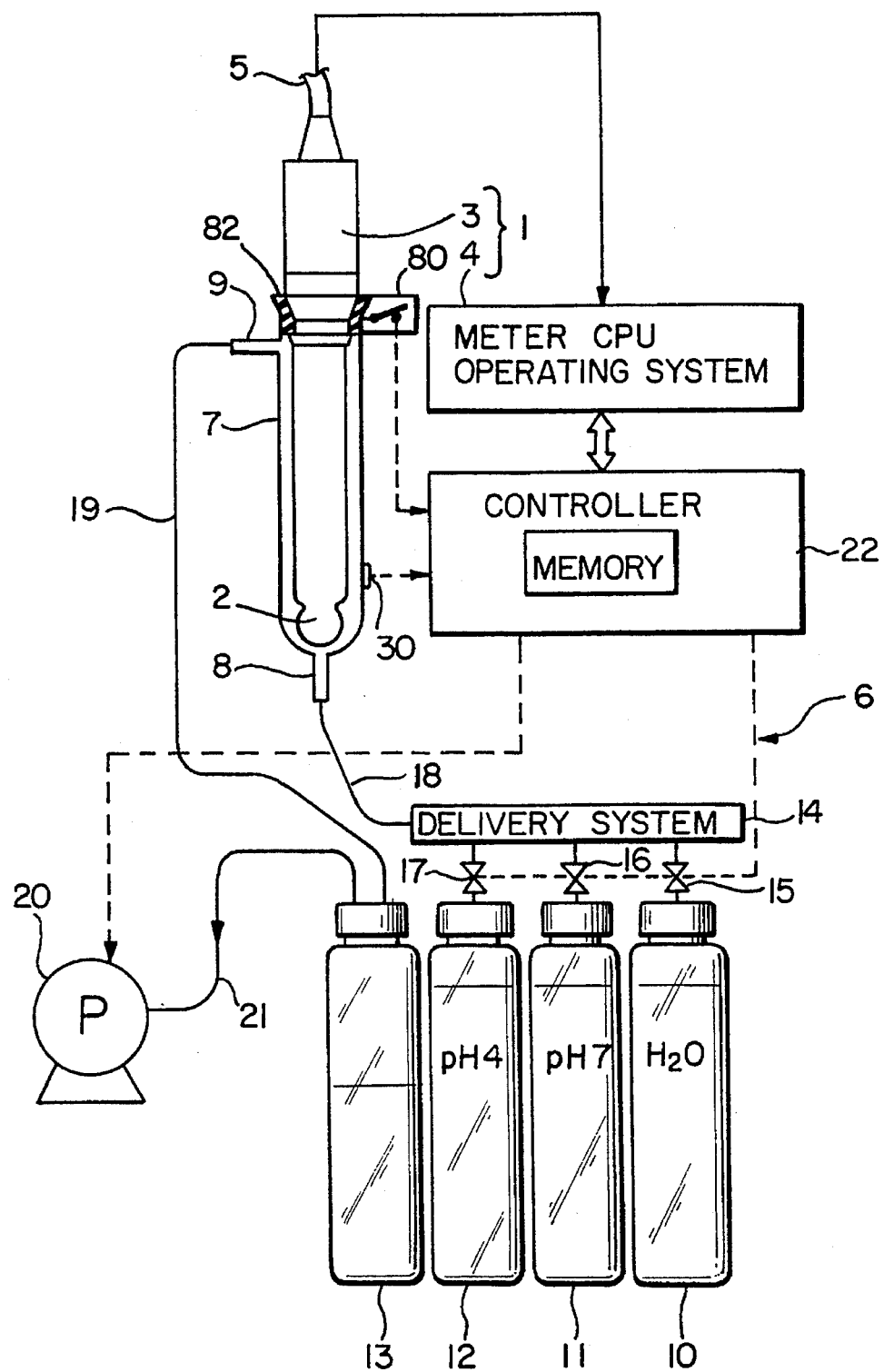
FIG. 1 discloses a schematic construction of an automatic calibrating apparatus according to one preferred embodiment of the present invention.

Referring to FIG. 1, a preferred embodiment of an automatic calibrating apparatus is disclosed. In this embodiment, a laboratory ion concentration meter, such as a pH meter 1, is schematically disclosed. The pH meter 1 includes a pH-measuring portion 3, such as an ion concentration measuring electrode 2 having a cylindrical configuration with a pointed end (lower end) thereof. A pH meter body 4, such as an ion concentration meter body, can include a CPU operating system. The electrode lead wire 5 extends from the upper end of the pH-measuring portion 3 so that a detected signal can be provided to the pH meter body 4. Although not shown in detail, the pH meter body 4 includes a CPU operating system so that any detected signal received from the signal cable 5 may be suitably processed to calculate a pH value of the solution, and further, to memorize and store that value and display the calculated pH value to an operator. The system can also print out the results of the measurement for permanent records. These features are common. Preferably, the pH meter body 4 includes output jacks or other electrical connectors that enable it to be connected to a controller 22, to be subsequently described.

The automatic calibrating apparatus 6 of the present invention includes a fluid-type chamber 7 that is capable of receiving and holding the pH-measuring portion 3 in a detachable manner. The chamber 7 is open at its upper portion thereof and closed at a lower portion thereof, and can be made of a transparent material such as glass or synthetic resins. The chamber 7 is of such a dimension that not only may the pH-measuring portion 3 be freely inserted into or drawn out through the opening thereof, but also, the pH-measuring portion 3 may be held, e.g., with an annular seal 82, so that it does not permit its electrode portion 2 to come into contact with either the bottom portion or the side portions of the chamber 7. It is also possible that an automatic switch mechanism (not shown) associated with the chamber opening and/or the pH-measuring portion 3 could be activated upon the insertion of the pH-measuring portion 3 to initialize the calibration system. Alternatively, a manual switch can be utilized to start the automatic calibration of the pH meter 1.

The chamber 7 has a liquid inlet 8 at the lower portion of the chamber 7, and a liquid discharge or outlet 9 at the upper portion of the chamber 7. A thermometer 30 can monitor the temperature of the fluid within the chamber 7. Preferably, the temperature monitor 30 is mounted at the lower portion of the chamber 7 adjacent the storage position of the electrode portion 2. A series of storage tanks or housings can store fluid such as the washing water tank 10 that houses washing water (for example, distilled and deionized pure water), while a pH standard solution can be housed in the containers 11 and 12. For example, a calibration solution pH 4 can be provided in housing 12, while a calibration solution pH 7 can be provided in housing 11. Finally, a waste liquid tank 13 can house any recovered waste liquid from the chamber 7.

A fluid control delivery system or changeover supply device 14 will supply the chamber 7 with, respectively, the washing water and the pH standard solutions in an appointed order that can be controlled by a computer program in the controller 22 or the meter body 4. In the preferred embodiment shown, the changeover supply device 14 is connected with the washing water tank 10 and the pH standard solution tanks 11 and 12 through closing valves 15, 16, and 17. These valves can, for example, be electrically controlled to open and close as desired. The changeover device 14 can either cause a positive pumping of the fluid into the chamber 7 or, if the chamber 7 is appropriately sealed, a suction pump can provide a negative pressure to draw the fluid into the chamber 7. A liquid supply pipe 18 is connected to the changeover device 14 and interconnects with the liquid inlet 8 of the chamber 7. A liquid recovery pipe 19 is connected to the liquid outlet 9 of the chamber 7, and is also connected to the waste liquid tank 13. In addition, a suction pump 20 is connected with the waste liquid tank 13 through a suction pipe 21. While not shown, appropriate filters or traps can be utilized to prohibit any contamination of the pump 20.

The controller 22 can control the automatic calibrating apparatus 6. This controller 22, although not shown in detail, can be constructed so as to both output and receive signals between it and the pH body 4, and further, to provide control signals for conducting the appointed calibration in accordance with a program instruction from a CPU that is included within a memory (not shown) in the pH meter body 4. Electrical connection lines are disclosed in FIG. 1 for monitoring and transmitting control signals to component parts of the system, such as valves 15–17 and the pump 20.

A schematic flow chart is shown in FIG. 5. In operation, the automatic calibrating system can be initialized at step 50, either through the insertion of the pH-measuring portion 3 into the chamber 7, for example, with a contact switch or a sensor switch, such as the switch 80, or the system can simply be activated by an ON button on the controller 22 (not shown). A decisional step can be utilized at step 52 to determine if the sensor is mounted in the container. If the sensor is not mounted in the container, then the system can turn off. If the sensor is found to be mounted in the chamber 7 for either express calibration procedures or simply to store the pH-measuring portion 3, then the controller 22 can activate the pump 20 at step 54 to introduce washing fluid when the changeover device 14 is also activated to open the valve 15. The valve 15 can subsequently be shut off after a predetermined time period or when a quantity of fluid has been introduced into the chamber 7. After an appropriate time period, the washing fluid can be discharged at step 56. At step 58, the controller 22 can activate the introduction of a calibrating fluid, such as the pH 4 calibration solution, from the supply tank 12. The valve 17 is then opened, and the calibrating fluid travels through the supply line 18 to the chamber 7. The controller 22 then coordinates with the pH meter body 4 to record an output signal of the sensor at step 60, while simultaneously measuring the temperature of the calibrating fluid with the thermometer 30 at step 62. The pump 20 can then cooperate to discharge the calibrating fluid into the sump or waste tank 13 at step 64. At step 66 a determination is made whether an additional calibration fluid is to be utilized. If so, steps 54–64 are repeated with the additional calibration solution, such as the pH solution 7 from the supply tank 11. In this regard, the valve 16 is then controlled by the controller 22. At step 68, a calibration procedure is automatically conducted on the basis of the recorded output signals and temperature signals. In addition, washing fluid can be introduced at step 70 to cleanse any remaining pH fluid that may have adhered to the pH-measuring portion 3. The washing fluid is then discharged at step 72 and the system is turned off. The pH meter 1 is then adequately calibrated and enabled to provide an accurate measurement of the pH value. The electrode portion 2 of the pH-measuring portion 3 can be used with confidence to determine an accurate pH measurement.

As can be appreciated, the pH-measuring portion 3 can be mounted in the chamber 7 during an off-time cycle other than the measurement of pH. Under such a condition, the calibration of the pH meter 1 can be automatically conducted in accordance with, for example, an instruction from the CPU system included in either the pH meter body 4 or a CPU operating system in the controller 22. The selection of which system is the master or the slave in a calibration cycle can obviously be selectively determined depending upon the pH instruments that are to be utilized. For example, it may be desirable that the controller 22 be the master unit and simply operate the pH meter body 4 at its discretion. Alternatively, the pH meter body 4 could be specifically designed to interface with an automatic controller 22 and, for purposes of economy can, in fact, drive the controller 22 with the controller 22 being the slave system with appropriately-stored information and operating systems to conduct the automatic calibration. The design of either one of these approaches is well known within the field of measurement instrumentation.

As an illustration of the operation of the preferred embodiment 1, the pH-measuring portion 3 of the pH meter 1 can be mounted on the chamber 7. At this time, an initial signal to start the calibration is output to the controller 22 in accordance with the program within the CPU included in the pH meter body 4. An instruction is then given to the pump 20 from the controller 22 wherein the pump 20 is switched on. Under this condition, the closing valve 15 is opened under an instruction from the controller 22 to introduce washing water or fluid into the chamber 7 to thereby wash the electrode portion 2 of the pH-measuring portion 3. This washing water is then recovered in the waste liquid tank 13 through the liquid recovery pipe 19. The closing valve 15 is then closed, and the closing valve 16 is opened under an instruction from the controller 22 to introduce the pH standard solution of pH 7 into the chamber 7. Additionally, at this time, a temperature of the pH standard solution within the chamber 7 is measured by means of a temperature sensor 30 provided in the chamber 7. The results of this measurement are put into the CPU of the pH meter body 4 through the controller 22. For example, if the measured temperature is 25° C., the pH meter body 4 can be adjusted by an adjusting program so that the output of the pH may become, for example, 6.86 (a standard value). After the adjustment, the pH standard solution of pH 7 within the chamber 7 is recovered in the waste liquid tank 13 through the liquid recovery pipe 19. The closing valve 16 is closed and the closing valve 15 is opened by an instruction from the controller 22 to introduce the washing water into the chamber 7 to again wash the electrode portion 2. Once again, the water used for the washing is recovered in the waste liquid tank 13 through the liquid recovery pipe 19. The closing valve 15 is closed and the closing valve 17 is opened by an instruction from the controller 22 to introduce the pH standard solution of pH 4 into the chamber 7. At this time, again the temperature of the pH standard solution within the chamber 7 is measured by means of the temperature sensor 30, and the results of the measurement are output to the CPU of the pH meter body 4 through the controller 22. Thus, if the measured temperature is, for example, 25° C., the pH meter body 4 is adjusted by an adjusting program so that the output of the pH may become, for example, 4.01 (a standard value). After the adjustment, the pH standard solution of pH 4 within the chamber 7 is recovered in the waste liquid tank 13 through the liquid recovery pipe 19.

As can be readily appreciated, this two-point calibration of the pH meter 1 can be automatically conducted without any attendance of an operating technician. This calibration can be put into practice at either a fixed time, or at regular intervals, by suitably setting the program to the CPU of the pH meter body 4.

Figure 2:
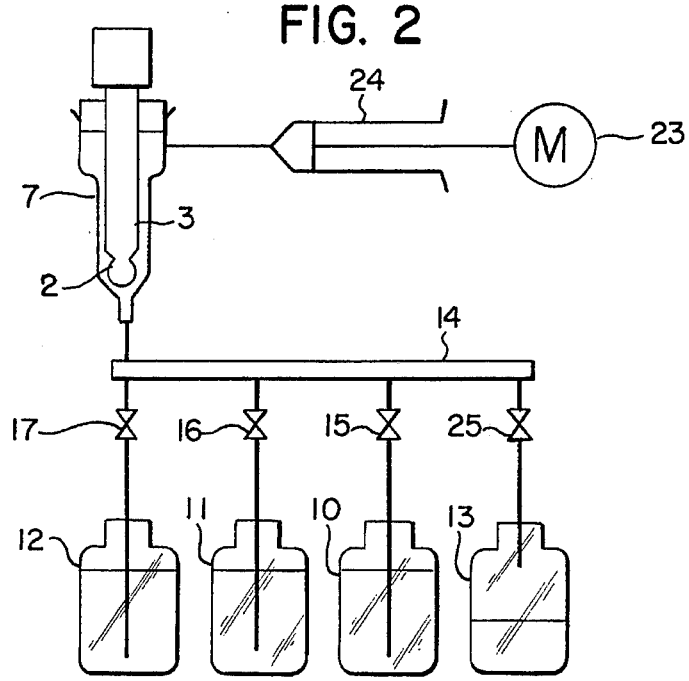
FIG. 2 discloses an alternative construction of an automatic calibrating apparatus.
Figure 4:
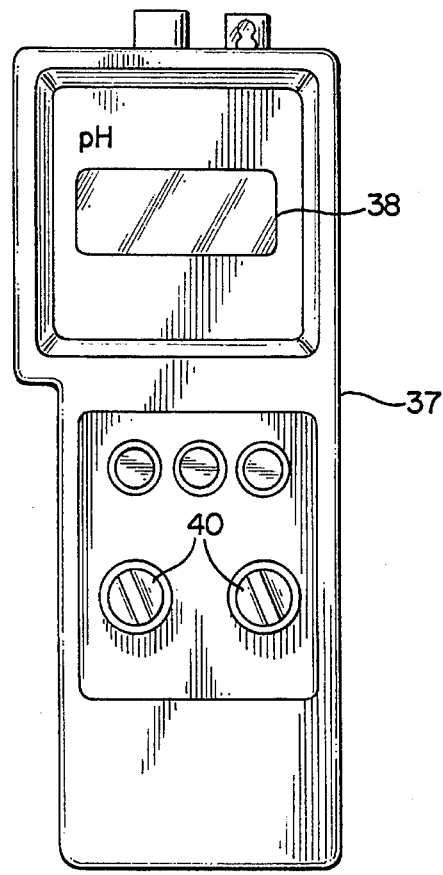
FIG. 4 is a plan view of a prior art laboratory pH meter with calibration knobs.
Figure 3A:
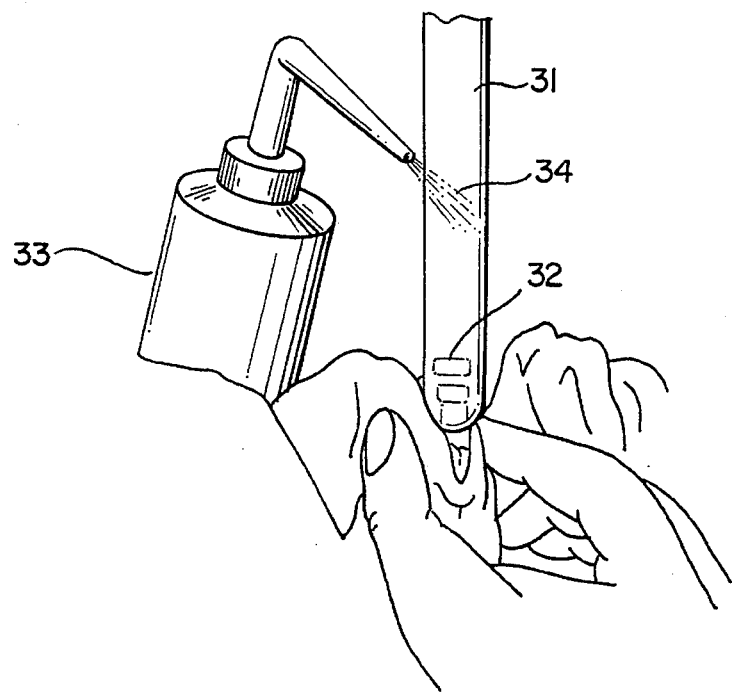
FIG. 3(A) is a perspective view of a prior art calibration procedure.
Figure 3B:
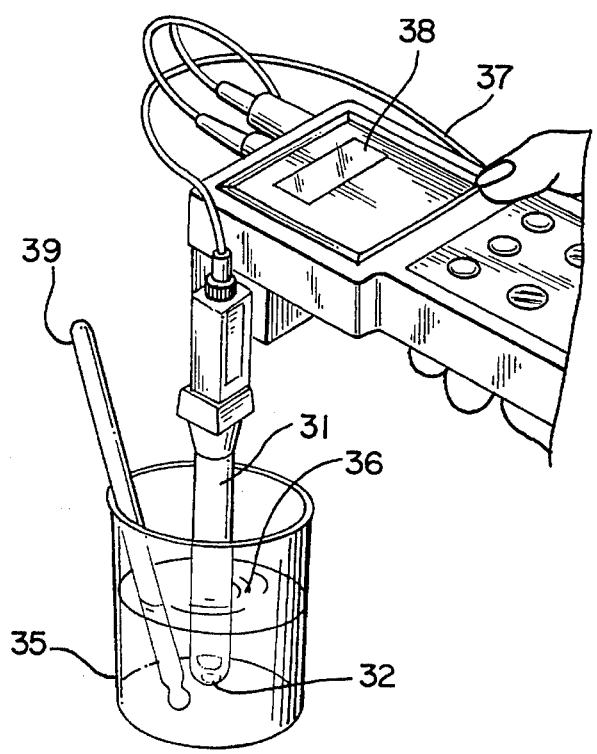
FIG. 3(B) is a perspective view of a prior art calibration procedure.

FIG. 2 discloses an alternative embodiment of an automatic calibrating apparatus. In this embodiment, a syringe 24 can be driven by a driving device motor 23 to evacuate the chamber 7 of any fluid. The specific calibration procedures in embodiment 2 are the same as with regard to embodiment 1, except that the washing water and the pH standard solution are removed by means of the syringe 24, and are also appropriately discharged by both the suction and pressure exerted by the motor 23 through the syringe 24. Once again, after the completion of the appointed washing and calibration, the respective liquids can be recovered in the waste liquid tank 13 upon appropriate activation of each of the valves, including the closing valve 25.

As can be readily appreciated, the present invention is not limited to the above embodiments. For example, the washing water and the pH standard solution may be transferred in a pneumatic manner. Additionally, the transfer of liquid may be carried out by means of various kinds of liquid pumps. Also, the changeover supply device 14 may be constituted by a electromagnetic valve or a rotary valve.

As mentioned above, although the controller 22 can conduct the calibration under instruction from a CPU system in the pH meter body 4, it is quite possible for an independent CPU system to be provided in the controller 22 to conduct the appointed calibration with direct instructions from that CPU system. The particular design objects can be a function of the economics and the particular requirements of the calibration system.

Finally, as can be appreciated, the present invention can be applied to the calibration of measurement instrumentation other than that of a pH meter. For example, other ion concentration meters can also enjoy the benefits of the present invention. In summary, the automatic calibration apparatus according to the present invention permits a laboratory ion concentration meter to be automatically calibrated in an unattended condition during an off-time period. Accordingly, calibration procedures are not required during a measurement, so that an appointed measurement of, for example, ion concentration, can be immediately carried out by the operator without wasting his or her time.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An automatic calibrating apparatus for supporting a separate portable measuring instrument with a portable sensor member comprising:

a hollow storage receptacle, independent of the measuring instrument, having a cavity with an entrance opening annular seal dimensioned to removably suspend a sensor member within the receptacle;

determining means for determining the insertion of the sensor member into the storage receptacle including a switch member;

an inlet conduit attached to the storage receptacle;

an outlet conduit attached to the storage receptacle wherein the inlet conduit is attached to the storage receptacle adjacent the bottom of the cavity and the outlet conduit is attached to the storage receptacle adjacent an upper side surface of the cavity;

means for storing separate fluids including a calibration solution and a washing solution;

means for selectively applying the fluids to the inlet conduit for delivery to the hollow storage receptacle;

means for activating a calibration procedure when enabled by the determination of the determining means that a sensor member is mounted in the storage receptacle, including means for coordinating which includes a controller operatively connectable to the separate portable measuring instrument, for coordinating first, the introduction of the washing solution into the receptacle and the subsequent removal of the washing solution, and second, the introduction of the calibration solution and removal of the calibration solution;

means for storing a measurement signal from the sensor member during the presence of the calibration solution;

means for automatically comparing the measurement signal with a stored reference value and providing a corresponding adjustment of the sensor member output signal; and means for removably connecting the controller with the measuring instrument to permit the corresponding adjustment of the sensor member output signal.

2. The invention of claim 1 further including means for measuring the temperature of the calibration solution.

3. The invention of claim 1 further including a second calibration solution.

4. The invention of claim 1 wherein the means for coordinating includes a series of valves operatively connected to the controller.

5. The invention of claim 1 further including a pump and a waste tank for receiving the removed washing solution and calibration solution when the pump is activated by the controller.

6. An automatic calibrating apparatus for calibrating a separate portable measuring instrument with a portable sensor member comprising:

a hollow storage receptacle, independent of the measuring instrument, having a cavity dimensioned to suspend a sensor member within the receptacle, including an upper aperture extending across the hollow storage receptacle and an annular seal configured to sealingly and removably receive a sensor member so that an electrode portion is positioned in close proximity to a bottom of the cavity receptacle;

an inlet conduit attached to the storage receptacle;

an outlet conduit attached to the storage receptacle of the cavity wherein the inlet conduit is attached to the storage receptacle adjacent the bottom of the cavity and the outlet conduit is attached to the storage receptacle adjacent an upper side surface of the cavity;

means for storing separate fluids including a calibration solution and a washing solution;

means for selectively applying the fluids to the inlet conduit for delivery to the hollow storage receptacle;

means for activating a calibration procedure, including means for coordinating which includes a controller operatively connectable to the separate portable measuring instrument, for coordinating first, the introduction of the washing solution into the receptacle and the subsequent removal of the washing solution, and second, the introduction of the calibration solution and removal of the calibration solution;

means for storing a measurement signal from the sensor member during the presence of the calibration solution;

means for automatically comparing the measurement signal with a stored reference value and providing a corresponding adjustment of the sensor member output signal; and means for removably connecting the controller with the measuring instrument to permit the corresponding adjustment of the sensor member output signal.

7. The invention of claim 6 further including means for measuring the temperature of the calibration fluid.

8. The invention of claim 6 further including means for storing a second calibration fluid.

9. The invention of claim 6 wherein the means for coordinating includes a series of Valves operatively connected to the controller.

10. The invention of claim 6 further including a pump and a waste tank for receiving the removed washing solution and calibration solution when the pump is activated by the controller.

* * * * *